United States Patent [19]
de Juan, Jr.

[11] Patent Number: 6,028,099
[45] Date of Patent: Feb. 22, 2000

[54] USE OF AN INHIBITOR OF THE PROTEIN TYROSINE KINASE PATHWAY IN THE TREATMENT OF CHOROIDAL NEOVASCULARIZATION

[75] Inventor: Eugene de Juan, Jr., Phoenix, Md.

[73] Assignee: John Hopkins University, School of Medicine, Baltimore, Md.

[21] Appl. No.: 09/041,601

[22] Filed: Mar. 13, 1998

[51] Int. Cl.[7] .......................... A67K 31/35; A67K 31/389
[52] U.S. Cl. ........................... 514/434; 514/456; 514/912
[58] Field of Search .................................. 514/434, 456, 514/912

[56] References Cited

U.S. PATENT DOCUMENTS 5,637,703  6/1997  Mazurek et al. .

FOREIGN PATENT DOCUMENTS

WO 97/30701  8/1997  WIPO .

OTHER PUBLICATIONS

Barnes, "Effect of Genistein on In Vitro and In Vivo Models of Cancer," *J. Nutr.* 125: 777S–783S (1995).

Barnes et al., "Biochemical Targets of the Isoflavone Genistein in Tumor Cell Lines," *PSEBM* 208: 103–108 (1995).

Burke, Jr. "Protein–Tyrosine Kinase Inhibitors," *Drugs of the Future* 17(2): 119–131 (1992).

Coward et al., "Genistein, Daidzein, and Their β–Blycoside Conjugates: Antitumor Isoflavones in Soybean Foods from American and Asian Diets," *J. Agric. Food Chem.* 41: 1961–1967 (1993).

Cunningham et al. "Synthesis and Biological Evalutation of a Series of Flavones Designed as Inhibitors of Protein Tyrosine Kinases," *Anti–Cancer Drug Design* 7: 365–384 (1992).

Filipeanu et al., "Multiple Effects of Tyrosine Kinase Inhibitors on Vascular Smooth Muscle Contraction," *European Journal of Pharmacology* 281(1): 29–35 (1995) (Abstract).

Fotsis et al., "Genistein, A Dietary Ingested Isoflavonoid Inhibits Cell–Proliferation and In–Vitro Angiogenesis," *Journal of Nutrition* 125(3): 790–797 (1995) (Abstract).

Fotsis et al., "Genistein, a Dietary–Derived Inhibitor of In Vitro Angiogensis," *PNAS USA* 90: 2690–2694 (1993).

Hayashi et al., "Activation of Protein Tyrosine Phosphorylation After Retinal Branch Vein Occlusion in Cats," *Investigative Ophthalmology & Visual Science* 38(2): 372–380 (1997).

Hayashi et al., "Increase of Protein Tyrosine Phosphorylation in Rat Retina After Ischemia–Reperfusion Injury," *Investigative Ophthalmology & Visual Science* 7(11): 2146–2156 (1996).

Hayashi et al., "Genistein, a Protein Tyrosine Kinase Inhibitor, Ameliorates Retinal Degeneration After Ischemia–Reperfusion Injury in Rat," *Investigative Ophthalmology & Visual Science* 38(6): 1193–1202 (1997).

Hayashi et al., "Role of Protein Tyrosine Phosphorylation in Rat Corneal Neovascualrization," *Graefe's Arch. Clin. Exp. Ophthalmol.* 235: 460–467 (1997).

Hayashi et al., "Genistein, A Protein Tyrosine Kinase Inhibitor, Ameliorates Retinal Degeneration After Ischemia–Reperfusion Injury in Rat," *Investigative Ophthalmology and Visual Science* 38(4): 489–B400 (1997) (Abstract).

Herman et al., "Soybean Phytoestrogen Intake and Cancer Risk," *J. Nutr.* 125: 757S–770S (1995).

Kennedy, "The Evidence of Soybean Products as Cancer Preventive Agents," *J. Nutr.* 125: 733S–742S (1995).

Kindy, "Inhibition of Tyrosine Phosphorylation Prevents Delayed Neuronal Death Following Cerebral Ischemia," *Journal of Cerebral Blood Flow and Metabolism* 13: 372–377 (1993).

Koroma et al., "Changes Associated With Tyrosine Phosphorylating During Short–Term Hypoxia in Retinal Microvascular Endothelial Cells In Vitro," *Journal of Cellular Biochemistry* 59: 123–132 (1995).

Koroma et al., "Phosphotyrosine Inhibition and Control of Vascular Endothelial Cell Proliferation by Genistein," *Biochemical Pharmacology* 48(4): 809–818 (1994).

Lamartiniere et al., "Neonatal Genistein Chemoprevents Mammary Cancer,"*PSEBM* 208: 120–123 (1995).

Levitzki et al., "Tyrosine Kinase Inhibition: An Approach to Drug Development," *Science* 267: 1782–1790 (1995).

Lu et al., "Effects of Soya Consumption for One Month on Steroid Hormones in Premenopausal Women: Implications for Breast Cancer Risk Reduction," *Cancer Epidemiology, Biomarkers & Prevention* 5: 63–70 (1996).

Moritoki et al., "Possible Involvement of Tyrosine Kinase in the LPS–Promoted Initiation of L–arginine–Induced Relaxation of Rat Aorta Mediated by Induction of $N_o$ Synthase," *Life Science* 57(11): PL125–130 (1995) (Abstract).

Ohira et al., "Retinal Ischemia and Cell Proliferation in the Rat: The Role of Soluble Mitogens," *Graefe's Arch Clin. Exp. Ophthalmol.* 228: 195–199 (1990).

Raines et al., "Biology of Atherosclerotic Plaque Formation: Possible Role of Growth Factors in Lesion Development and the Potential Impact of Soy," *Journal of Nutrition* 125(3 Suppl.): 624S–630S (1995) (Abstract).

(List continued on next page.)

*Primary Examiner*—Zohreh Fay
*Attorney, Agent, or Firm*—Leydig, Voit & Mayer, Ltd.

[57] ABSTRACT

The present invention is directed to a method for the prophylactic and therapeutic treatment of choroidal neovascularization. The method involves the administration of an inhibitor of the protein tyrosine kinase pathway to an animal, such as a mammal, in particular a human, in an amount sufficient to treat the choroid for neovascularization prophylactically or therapeutically. The inhibitor of the protein tyrosine kinase pathway is preferably genistein or an analogue or prodrug thereof or a pharmaceutically acceptable salt of any of the foregoing.

36 Claims, No Drawings

OTHER PUBLICATIONS

Steele et al., "Cancer Chemoprevention Agent Development Strategies for Genistein," *J. Nutr.* 125: 713S–716S (1995).

Steusloff et al., "Modulation of Ca2+ Sensitivity in Smooth Muscle by Genistein and Protein Tyrosine Phosphorylation," *Archives of Biochemistry & Biophysics* 320(2): 236–242 (1995) (Abstract).

Wilcox et al., "Thrombic Mechanisms in Atheroscelorsis: Potential Impact of Soy Proteins," *Journal of Nutrition* 125(3): 631S–638S (1995) (Abstract).

Xiong et al., "Modulation of Ca(2+)–activated K+ Channel Activity by Tyrosine Kinase Inhibitors in Vascular Smooth Muscle Cell," *European Journal of Pharmacology* 290(2): 117–123 (1995) (Abstract).

USE OF AN INHIBITOR OF THE PROTEIN TYROSINE KINASE PATHWAY IN THE TREATMENT OF CHOROIDAL NEOVASCULARIZATION

TECHNICAL FIELD OF THE INVENTION

The present invention relates to a method for the prophylactic and therapeutic treatment of choroidal neovascularization.

BACKGROUND OF THE INVENTION

Choroidal neovascularization is the development of new blood vessels in the vascular choroid, which is comprised of the choriocapillaris and larger choroidal vessels. The choriocapillaris, which is a collection of richly perfused sinusoids, is located adjacent to the retinal pigmented epithelium and Bruch's membrane in the eye. It provides vascular support to the outer retina, including the pigmented epithelium and photoreceptors. The choriocapillaris atrophies with age-related macular degeneration, retinitis pigmentosa, and after removal of choroidal neovascular membranes in exudative age-related macular degeneration, presumed ocular histoplasmosis syndrome, and high myopia and, thus, is believed to contribute to the poor vision associated with such conditions.

One possible cause of the atrophy of the choriocapillaris is the degeneration of the pigmented epithelium. Clinically, the degeneration of the pigmented epithelium has been observed to precede choriocapillaris atrophy. Experimental studies of the choriocapillaris, however, have been mixed. Some researchers have reported that selective destruction of the pigmented epithelium, such as by laser burns, administration of sodium iodate or debridement, have led to choriocapillaris atrophy (Henkind et al., *Trans. Ophthal. Soc. U.K.* 103: 444–447 (1983); Korte et al., *Invest. Ophthalmol. Vis. Sci.* 25: 1135–1145 (1984); and Heriot et al., *Graefes Arch. Clinical Exp. Ophthalmol.* 230: 91–100 (1992)), whereas other researchers have reported that such selective destruction has led to atrophy followed by regeneration and differentiation of the choriocapillaris (Korte et al., *Int. Rev. Cytology* 152: 223–263 (1994); Pollack et al., *Acta Anat.* 143: 151–159 (1992); Pollack et al., *Invest. Ophthalmol. Vis. Sci.* 31: 890–898 (1990); Mancini et al., *Invest. Ophthalmol. Vis. Sci.* 27: 336–345 (1986); and Bums et al., *Curr. Eye Res.* 9: 863–873 (1992)). Hereditary degeneration of the pigmented epithelium has been shown to cause loss of the choriocapillaris in the Royal College of Surgeon's rat (Caldwell, *Curr. Eye Res.* 8: 907–921 (1989); and May et al., *Exp. Eye Res.* 63: 75–84 (1996)). Accordingly, the mechanisms by which the retinal pigmented epithelium regulates and maintains the choriocapillaris are not well understood. However, atrophy of the choriocapillaris is suspected to lead to choroidal neovascularization.

Currently, choroidal neovascularization is most commonly identified by fluorescein angiography, alone or in combination with indocyanine-green angiography, and well-defined choroidal neovascular lesions are treated by laser photocoagulation. Unfortunately, laser photocoagulation does not prevent neovascularization from persisting or recurring. Sometimes, when choroidal neovascularization occurs in association with exudative age-related macular degeneration, the choroidal neovascular complex is surgically removed. However, such subretinal surgery is hazardous and is generally only considered in functionally blind patients.

Therefore, there remains a great need for a method for the effective prophylactic and therapeutic treatment of choroidal neovascularization. Accordingly, it is a principal object of the present invention to provide a method of prophylactically and therapeutically treating choroidal neovascularization, such as that resulting from macular degeneration, e.g., age-related macular degeneration, recurrent or persistent choroidal neovascularization associated with treatments such as laser photocoagulation, photodynamic therapy and surgical removal of choroidal neovascularization, and choroidal neovascularization due to histoplasmosis, pathological myopia and other conditions. This and other objects of the present invention will become apparent from the detailed description provided herein.

BRIEF SUMMARY OF THE INVENTION

The present invention is directed to a method for the prophylactic and therapeutic treatment of choroidal neovascularization. The method involves the administration of an inhibitor of the protein tyrosine kinase pathway. Preferably, the inhibitor of the protein tyrosine kinase pathway is a compound of formula:

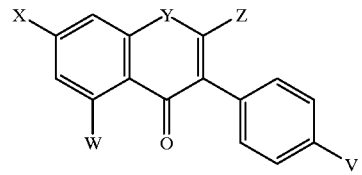

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

DETAILED DESCRIPTION OF THE INVENTION

The present invention is predicated on the discovery that an inhibitor of the protein tyrosine kinase pathway, specifically genistein, is effective in the prevention of choroidal neovascularization. Accordingly, the present invention provides a method for the prophylactic and therapeutic treatment of choroidal neovascularization. By "prophylactic" is meant the protection, in whole or in part, against choroidal neovascularization. By "therapeutic" is meant the amelioration of choroidal neovascularization, itself, and the protection, in whole or in part, against further choroidal neovascularization. The present inventive method is particularly useful in the treatment of choroidal neovascularization due to macular degeneration, such as age-related macular degeneration. However, the present inventive method is also useful in the treatment of choroidal neovascularization, including persistent and recurrent choroidal neovascularization, which has been treated, is being treated or will be treated with laser photocoagulation or photodynamic therapy, and in the treatment of choroidal neovascularization that persists or recurs after surgical removal of an existing choroidal neovascularization. In addition, the present inventive method is useful in the treatment of choroidal neovascularization due to histoplasmosis and pathological myopia as well as choroidal neovascularization that results from angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida* endophthalmitis, extrapapillary hamartomas of the retinal pigmented epithelium, fundus flavimaculatus, idiopathic, macular hole, malignant melanoma, membranproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctate inner choroidopathy, radiation retinopathy, retinal cryoinjury, retinitis pigmentosa, retinochoroidal coloboma, rubella, sarcoidosis, serpiginous or geographic choroiditis, subretinal fluid drainage, tilted disc syndrome, *Taxoplasma* retinochoroiditis, tuberculosis, or Vogt-Koyanagi-Harada syndrome, among others.

The method comprises the administration of an inhibitor of the protein tyrosine kinase pathway in an amount sufficient to treat the choroid for neovascularization prophylactically or therapeutically. Any inhibitor of the protein tyrosine kinase pathway can be used in the method of the present invention as long as it is safe and efficacious. Herein, "PTK inhibitor" will be used to refer to such compounds and is intended to encompass all compounds that affect the protein tyrosine kinase pathway at any and all points in the pathway.

Preferably, the PTK inhibitor is genistein (5,7-dihydroxy-3-(4-hydroxyphenyl)-4H-1-benzopyran-4-one) or a pharmaceutically acceptable, protein tyrosine kinase pathway-inhibiting analogue or prodrug thereof or a pharmaceutically acceptable salt of any of the foregoing. Accordingly, the PTK inhibitor can be a compound of the following formula:

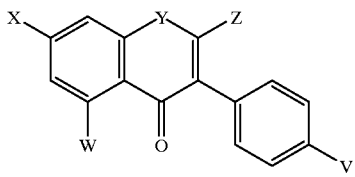

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

The prodrug can be any pharmaceutically acceptable prodrug of genistein, a protein tyrosine kinase pathway-inhibiting analogue of genistein, or a pharmaceutically acceptable salt of either of the foregoing. One of ordinary skill in the art will appreciate, however, that the prodrug used must be one that can be converted to an active PTK inhibitor in or around the choroid. A preferred prodrug is a prodrug that increases the lipid solubility of genistein, a protein tyrosine kinase pathway-inhibiting analogue of genistein, or a pharmaceutically acceptable salt of either of the foregoing. A preferred prodrug is one in which one or more of V, W and X are independently derivatized with an ester, such as pivalic acid.

Compounds of the above formula are widely available commercially. For example, genistein is available from LC Laboratories (Woburn, Mass.). Those compounds that are not commercially available can be readily prepared using organic synthesis methods known in the art.

Whether or not a particular analogue, prodrug or pharmaceutically acceptable salt of a compound in accordance with the present invention can treat choroidal neovascularization prophylactically or therapeutically can be determined by its effect in the rabbit model used in Example 1. Alternatively, analogues, prodrugs and pharmaceutically acceptable salts of inhibitors of the protein tyrosine kinase pathway can be tested by induced choroidal neovascularization in the primate model and in vitro endothelial cell proliferation assay in the corneal burn neovascularization model, which can be quantitated as an assay.

The PTK inhibitor can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable (see, e.g., U.S. Pat. Nos. 5,384,333 and 5,164,188).

An advantage of genistein is that it is very safe and efficacious. For example, when genistein was orally administered to Zucker diabetic fatty rats, genistein was found to be nontoxic to the retina at dosages ranging from 75 mg/kg/day to 300 mg/kg/day over a period of six months as measured by electroretinography. In addition, oral administration of genistein was found to have no effect on food intake and body weight for male and female rats. Also, no effect of orally administered genistein was found with respect to the weight of the ovaries and the uterus in female rats.

The PTK inhibitor, which is preferably genistein, a protein tyrosine kinase pathway-inhibiting analogue of genistein, a protein tyrosine kinase pathway-inhibiting prodrug of genistein, or a pharmaceutically acceptable salt of any of the foregoing, can be administered in accordance with the present inventive method by any suitable route. Suitable routes of administration include systemic, such as orally or by injection, topical, periocular (e.g., subTenon's), subconjunctival, intraocular, subretinal, suprachoroidal, and retrobulbar. The manner in which the PTK inhibitor is administered is dependent, in part, upon whether the treatment of choroidal neovascularization is prophylactic or therapeutic. The manner in which the PTK inhibitor is administered for therapeutic treatment of choroidal neovascularization is dependent, in part, upon the cause of the choroidal neovascularization.

For example, given that macular degeneration is the leading cause of choroidal neovascularization, the PTK inhibitor can be administered prophylactically as soon as macular degeneration is detected. For the prophylactic treatment of choroidal neovascularization that can result from macular degeneration, the PTK inhibitor is preferably administered orally or systemically. Oral or systemic administration is preferred in the prophylactic treatment of choroidal neovascularization that can result from macular degeneration because, once one eye is affected, the other eye is at risk (up to 19% per year).

The PTK inhibitor is preferably administered intraocularly for the prophylactic or therapeutic treatment of persistent or recurrent choroidal neovascularization treated with laser photocoagulation and photodynamic therapies. The prophylactic or therapeutic treatment of persistent or recurrent choroidal neovascularization treated with surgical removal of an existing choroidal neovascularization also preferably involves intraocular administration of the PTK inhibitor.

The prevention or treatment of choroidal neovascularization associated with histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous Candida endophthalmitis, extrapapillary hamartomas of the retinal pigmented epithelium, fundus flavimaculatus, idiopathic, macular hole, malignant melanoma, membranproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctate inner choroidopathy, radiation retinopathy, retinal cryoinjury, retinitis pigmentosa, retinochoroidal coloboma, rubella, sarcoidosis, serpiginous or geographic choroiditis, subretinal fluid drainage, tilted disc syndrome, *Taxoplasma* retinochoroiditis, tuberculosis, or Vogt-Koyanagi-Harada syndrome, among others, involves the administration of the PTK inhibitor by any suitable method, although intraocular administration is often preferred.

The PTK inhibitor is preferably administered as soon as possible after it has been determined that an animal, such as a mammal, specifically a human, is at risk for choroidal neovascularization (prophylactic treatment) or has begun to develop choroidal neovascularization (therapeutic treatment). Treatment will depend, in part, upon the particular PTK inhibitor used, the amount of the PTK inhibitor administered, the route of administration, and the cause and extent, if any, of choroidal neovascularization realized.

One skilled in the art will appreciate that suitable methods of administering a PTK inhibitor, which is useful in the present inventive method, are available. Although more than one route can be used to administer a particular PTK inhibitor, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular PTK inhibitor employed, the age, species, condition or disease state, and body weight of the animal, as well as the amount of choroid about to be affected or actually affected by neovascularization. The size of the dose also will be determined by the route, timing and frequency of administration as well as the existence, nature, and extent of any adverse side effects that might accompany the administration of a particular PTK inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg/day, if administered systemically. Intraocular administration typically will involve the administration of from about 0.1 mg total to about 5 mg total, preferably from about 0.5 mg total to about 1 mg total. A preferred concentration for topical administration is 100 $\mu$M.

Compositions for use in the present inventive method preferably comprise a pharmaceutically acceptable carrier and an amount of a PTK inhibitor sufficient to treat choroidal neovascularization prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the PTK inhibitor can be formulated as polymeric compositions, inclusion complexes, such as cyclodextrin inclusion complexes, liposomes, microspheres, microcapsules and the like (see, e.g., U.S. Pat. Nos. 4,997,652, 5,185,152 and 5,718,922).

The PTK inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the PTK inhibitor and one which has no detrimental side effects or toxicity under the conditions of use.

The choice of excipient will be determined in part by the particular PTK inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, 4th ed., pages 622–630 (1986)). It is preferred that such injectable compositions be administered intramuscularly, intravenously or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), e.g., a mechanical reservoir, an intraocular device or an extraocular device with an intraocular conduit (e.g., 100$\mu$–1 mm in diameter), or an implant or a device comprised of a polymeric composition as described above, can be used.

The present inventive method also can involve the co-administration of other pharmaceutically active compounds. By "co-administration" is meant administration before, concurrently with, e.g., in combination with the PTK inhibitor in the same formulation or in separate formulations, or after administration of a PTK inhibitor as described above. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, anti-oxidants, e.g., carotenoids (such as a xanthophyll carotenoid like zeaxanthin or lutein), and micronutrients can be co-administered. In addition, other types of inhibitors of the protein tyrosine kinase pathway, which include natural protein tyrosine kinase inhibitors like quercetin, lavendustin A, erbstatin and herbimycin A, and synthetic protein tyrosine kinase inhibitors like tyrphostins (e.g., AG490, AG17, AG213 (RG50864), AG18, AG82, AG494, AG825, AG879, AG1112, AG1296, AG1478, AG126, RG13022, RG14620 and AG555), dihydroxy- and dimethoxybenzylidene malononitrile, analogs of lavendustin A (e.g., AG814 and AG957), quinazolines (e.g., AG1478), 4,5-dianilinophthalimides, and thiazolidinediones, can be co-administered with genistein or an analogue, prodrug or pharmaceutically acceptable salt thereof (see Levitzki et al., *Science* 267: 1782–1788 (1995); and Cunningham et al., *Anti-Cancer Drug Design* 7: 365–384 (1992)). In this regard, potentially useful derivatives of genistein include those set forth in Mazurek et al., U.S. Pat. No. 5,637,703. Neutralizing proteins to growth factors, such as a monoclonal antibody that is specific for a given growth factor, e.g., VEGF (for an example, see Aiello et al., *PNAS USA* 92: 10457–10461 (1995)), or phosphotyrosine (Dhar et al., *Mol. Pharmacol.* 37: 519–525 (1990)), can be co-administered. Other various compounds that can be co-administered include inhibitors of protein kinase C (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNFα, an anti-proliferative peptide, e.g., SPARC and prolferin-like peptides, a glutamate receptor antagonist, aminoguanidine, an angiotensin-converting enzyme inhibitor, e.g., angiotensin II, calcium channel blockers, Ψ-tectorigenin, ST638, somatostatin analogues, e.g., SMS 201–995, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638 (Asahi et al., *FEBS Letter* 309: 10–14 (1992)), thalidomide, nicardipine hydrochloride, aspirin, piceatannol, staurosporine, adriamycin, epiderstatin, (+)-aeroplysinin-1, phenazocine, halomethyl ketones, anti-lipidemic agents, e.g., etofibrate, chlorpromazine and spinghosines, aldose reductase inhibitors, such as tolrestat, SPR-210, sorbinil or oxygen, and retinoic acid and analogues thereof (Burke et al., *Drugs of the Future* 17(2): 119–131 (1992); and Tomlinson et al., *Pharmac. Ther.* 54: 151–194 (1992)). Selenoindoles (2-thioindoles) and related disulfide selenides, such as those described in Dobrusin et al., U.S. Pat. No. 5,464,961, are useful protein tyrosine kinase inhibitors. Recombinant interferon α2A can be co-administered to treat choroidal neovascularization, such as that resulting from age-related macular degeneration.

EXAMPLE

The following example further illustrates the present invention but, of course, should not be construed as in any way limiting its scope.

Example 1

This example demonstrates that genistein significantly inhibits choriocapillary regeneration without affecting wound healing of the retinal pigmented epithelium.

Eighty-one adult pigmented rabbits, each of which weighed 4–5 lbs., were evaluated by color fundus photography and fluorescein angiography. The rabbits were anesthetized with ketamine (30 mg/kg body weight), xylazine (5 mg/kg body weight) and topical proparacaine hydrochloride and their pupils were dilated with 2.5% phenylephrine hydrochloride and 1% tropicamide. Color fundus photography was performed with 100 ASA color film on a Topcon TRC-50FT retinal camera. Fluorescein angiography was performed using 400 ASA black and white film on a Topcon TRC-50FT retinal camera using barrier and exiter filters. Sodium fluorescein (0.15 ml of a 10% solution) was injected into the ear vein before taking pictures. Early and late phases were recorded up to five minutes after injection.

Then, the rabbits were divided into treatment and positive and negative control groups. The treatment group received genistein, whereas the positive control group received cycloheximide, which is an inhibitor of protein synthesis and apoptosis, and the negative control group received dimethyl sulfoxide (DMSO), which was used as a base to dilute and preserve genistein. Nine normal fellow eyes were used to obtain normal values for comparison (herein referred to as "preoperative values").

Genistein (freshly prepared as a 90 μM solution in DMSO and lactated ringer's solution and protected from exposure to light), cycloheximide (20 μg/ml in lactated ringer's solution), and DMSO (in lactated ringer's solution) were administered to the rabbits by intravitreal injection of 0.1 ml with a 30 gauge needle at 3.5 mm from the limbus in the superotemporal quadrant, with adequate paracentesis to prevent increased intraocular pressure, using venous pulsations as a guide. Twenty four hours later, the rabbits were anesthetized as described above and their pupils were dilated, also as described above.

Then, the pigmented epithelia of the rabbits were surgically debrided in accordance with procedures that conform to the resolution of The Association for Research in Vision and Ophthalmology (ARVO) on the use of animals in ophthalmic and vision research. Specifically, each rabbit was positioned under a Storz operating microscope, its globe was exposed, and a superior 180° conjunctival peritomy was performed. Two sclerotomies were made at 3.5 mm from the limbus in the superotemporal and superonasal quadrants after diathermy and mattress suturing with 6.0 vicryl (Ethicon, Somerville, N.J.). A vitrectomy was performed using a vitreous cutter. Retinal detachment was induced in the area centralis with a jet of irrigating solution (lactated ringer's solution) through a 30 gauge cannula. A retinectomy was performed over area 3DD. The retinal pigmented epithelium was debrided with a 20 gauge silicone brush, taking care not to disturb the underlying Bruch's membrane. The debrided pigmented epithelium was aspirated from the vitreous cavity with the ocutome in aspiration mode. The sclerotomy ports were closed at the end of the surgery. An ointment comprising prednisolone acetate and gentamycin sulfate was applied to the globe. The rabbits were returned to their cages after they regained consciousness.

At one, seven, fourteen and thirty days post-surgery, the eyes, upon which surgery was performed, were examined by color fundus photography and fluroescein angiography as described above. Color fundus photography revealed minimal exudate on the first day after surgery that cleared by seven days after surgery, with varying pigmented epithelial regeneration from the periphery to the center. Thirty days post-surgery, pigmented epithelial regeneration was more complete with appearance of varying pigmentation and scarring. The degree of exudation, pigmented epithelial regeneration and scar formation were not significantly different between the groups on color fundus photography.

Fluorescein angiography revealed leakage of the wound area one day after surgery for all groups. However, by seven days post-surgery, no leakage was observed, possibly due to retinal pigmented epithelial regeneration, and the wound areas remained nonleaky fourteen and thirty days post-surgery. Regeneration of the retinal pigmented epithelia was observed as progressive blocked fluorescence from the periphery to the center, with no differences observed between groups. Significant choriocapillary atrophy was observed in the group treated with genistein at fourteen days and thirty days post-surgery in comparison to the control groups.

In addition, nine rabbits from each group were euthanised at one, seven, fourteen and thirty days post-surgery. The rabbits were sedated as described above and euthanised by a single intravenous overdose of pentobarbital sodium. Three eyes from each group of nine rabbits were subjected to vascular cast preparation to examine choroidal vascular changes, whereas three eyes from each group of nine rabbits were subjected to scanning electron microscopic examination of the pigmented epithelium, and three eyes from each group of nine rabbits were subjected to histological evaluation by light and electron microscopy.

After those rabbits, which were to be subjected to vascular cast preparation, were anesthetized as described above, their carotid arteries were isolated on both side and perfused with 500 ml of heparinized lactated ringer's solution. Then, the rabbits were euthanised as described above and mercox solution (Ladd Research Industries, Burlington, Vt.) was injected through the isolated carotids. The eyes were enucleated, the anterior segments were separated, and the posterior segments were bleached in 0.1 mol KOH. After the posterior segments were bleached, the retinal vessels were separated from the choroidal vasculature. The choroidal vascular casts were rinsed in water and air-dried. The casts were mounted on aluminum stubs (Ted Pella, Inc.) and sputter-coated with gold palladium prior to scanning electron microscopy (JOEL JSM-840 A scanning electron microscope). The wound area was recorded at 25× and 400× magnifications. Three representative areas in the wound in each specimen were recorded at 400× magnification for quantitative analysis of the choroidal vascular bed. The micro plan 2 computer program was used to measure the area of the choroidal vascular bed in each photograph. Areas of individual segments were measured and summed in each photograph after adjusting the magnification factor. The resultant values in each group at one, seven, and thirty days post-surgery were tabulated and analyzed by paired student t-test in comparison to the pre-operative values and between the groups and time intervals. p values less than 0.05 were taken as significant.

Choriocapillary atrophy was observed one day post-surgery and continued at seven days post-surgery. However, regeneration appeared to reach near normal, i.e., pre-operative levels, by thirty days post-surgery in the control group. Those groups that were treated with genistein or cycloheximide showed sparing of capillary atrophy at one day post-surgery and the condition became more severe seven days post-surgery in comparison to the DMSO-treated group. The group treated with genistein continued to show severe choriocapillary atrophy thirty days post-surgery. Choriocapillaries appeared to regenerate by thirty days post-surgery.

Quantitative analysis of the choroidal vascular bed in the wound area after debridement of the retinal pigmented epithelia revealed significant choriocapillary atrophy in the DMSO-treated group at one day post-surgery (0.007) and seven days post-surgery (0.0001) over pre-operative levels. At thirty days post-surgery, there was no significant difference over pre-operative levels (0.07) for the DMSO-treated group, signifying regeneration of choriocapillaries after initial atrophy as shown in Table I. There was significant inhibition of choriocapillary regeneration in the genistein-treated group at thirty days post-surgery compared to the DMSO-treated group (0.012) and the cycloheximide-treated group (0.062) and at seven days post-surgery compared to the DMSO-treated group (0.02). Inhibition of choriocapillary regeneration was significant with cycloheximide at seven days post-surgery as compared to the DMSO-treated group (0.039); however, by thirty days post-surgery, it was not significant (0.24). One day post-surgery, the DMSO-treated group showed significant atrophy in comparison to the genistein-treated group (0.016). The difference in area was not significant in the cycloheximide-treated group in comparison to the genistein-treated group (0.18) and the DMSO-treated group (0.34), signifying sparing of atrophy in the genistein-treated group at one day post-surgery. The sparing of atrophy was present in the cycloheximide-treated group but it was not statistically significant (Table I).

TABLE I

|  |  | Preop | Day 1 | Day 7 | Day 30 |
| --- | --- | --- | --- | --- | --- |
| Control | Average (n = 9) | 0.05811 | 0.03963[a] | 003842*[a] | 0.0465 |
|  | Std. dev | 0.00062 | 0.00239 | 0.00098 | 0.0051 |
| Genistein | Average (n = 9) | 0.05811 | 0.04979* | 0.03223* | 0.01871[a] |
|  | Std. dev | 0.00062 | 0.00402 | 0.00254 | 0.00168 |
| Cycloheximide | Average (n = 9) | 0.05811 | 0.04369[a] | 0.02837[a] | 0.03711[a] |
|  | Std. dev | 0.00062 | 0.00473 | 0.00326 | 0.00681 | all values given in $mm^2$
P value <0.05 between groups*
between time periods[a]

Those eyes, the retinal pigmented epithelia of which were to be examined by scanning electron microscopy, were enucleated, followed by dissection of the anterior segment, and immersion overnight in 2% gluteraldehyde and 2% paraformaldehyde in 0.1 mol phosphate buffer at 4° C. The posterior segments of the eyes were trimmed down to the area of interest, post-fixed for 90 min in 1% osmium tetroxide in phosphate buffer, acetone dehydrated, and covered with tetramethylsilane. The tissues were mounted on aluminum stubs (Ted Pella, Inc.) and sputter-coated with gold palladium prior to scanning electron microscopy (JOEL JSM-840 A scanning electron microscope).

At one day post-surgery, scanning electron microscopy did not reveal any residual or regenerating retinal pigmented epithelia. Bruch's membrane was intact and was covered by transudate in some specimens. By seven days post-surgery, retinal pigmented epithelia covered the whole wound area in all groups. However, in the genistein-treated group, the retinal pigmented epithelia appeared less mature in comparison to the DMSO- and cycloheximide-treated groups. By thirty days post-surgery, the retinal pigmented epithelia appeared nearly mature in the DMSO-treated group in comparison to the genistein- and cycloheximide-treated groups, although all groups showed central immature retinal pigmented epithelial cells as compared to cells present in intermediate and marginal areas.

Those eyes, which were to be examined by light and electron microscopy, were enucleated, the anterior segments dissected, and immersed overnight as described for those eyes that were to be examined by scanning electron microscopy. The specimens were then dissected and half of the wound area was archived and the other half was dissected into two parts, post fixed for 2 hrs in 2% osmium tetroxide in phosphate buffer, alcohol-dehydrated, and embedded in epoxy resin. Sections (2μ) were stained with toludine blue for light microscopy. Thin sections were stained with lead citrate and uranyl acetate for electron microscopy.

Transudate and few red blood cells were observed by light microscopy in specimens from all three groups at one day post-surgery. Bruch's membrane was intact in all specimens and retinal pigmented epithelia appeared intact in all groups.

Electron microscopy revealed choriocapillaries with endothelial fenestrations on the retinal pigmented epithelium side with good apposition of the basement membrane. Choroidal capillary histology was comparable to the unoperated eye. Debridement of the retinal pigmented epithelia appeared complete and the Bruch's membrane appeared intact in all specimens. By seven days post-surgery, the pigmented epithelia appeared to cover the wound area in all of the specimens upon light microscopy. Upon electron microscopy, however, early changes of maturation, i.e., apical pigment granules, basal villi and zonulae occludence, and multiple layers of retinal pigmented epithelium were observed. The lumens of the choriocapillaries appeared narrow, with fewer vascular fenestrations and loose basement membranes, indicating choriocapillary atrophy in all groups. By thirty days post-surgery, the pigmented epithelium appeared to be multi-layered with areas of atrophy in all specimens. Electron microscopy revealed changes of maturation were similar to specimens at seven days post-surgery, with areas of acinar atrophy of the pigmented epithelium. In the DMSO- and cycloheximide-treated control groups, choriocapillaries appeared to be regenerating with new basement membrane formation and good vascular cavities. However, choriocapillaries were absent from the genistein-treated group.

These results show that loss of the retinal pigmented epithelium causes initial atrophy and subsequent regeneration of choriocapillaries as wound healing of the retinal pigmented epithelium occurs and that genistein significantly inhibits choriocapillary regeneration without affecting wound-healing of the retinal pigmented epithelium. Choriocapillary regeneration reached near normal state by thirty days post-surgery in the DMSO-treated control group. In contrast, genistein treatment inhibited choriocapillary regeneration significantly at seven days post-surgery compared to the DMSO-treated control group (0.02) and thirty days post-surgery compared to the DMSO- (0.013) and cycloheximide-treated control groups (0.062).

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of prophylactically or therapeutically treating an animal for choroidal neovascularization, which method comprises administering to said animal a compound of formula:

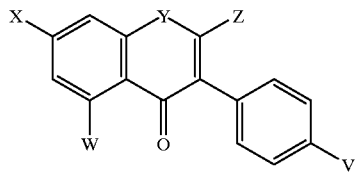

wherein V, W and X are selected from the group consisting of hydro, alkoxy, hydroxyl, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl, or a prodrug or pharmaceutically acceptable salt thereof, in an amount sufficient to treat said animal for choroidal neovascularization prophylactically or therapeutically.

2. The method of claim 1, wherein the halo group is selected from the group consisting of fluorine, chlorine and bromine.

3. The method of claim 1, wherein the ester is a $C_1$–$C_6$ ester.

4. The method of claim 1, wherein the ether is a $C_{1-6}$ ether.

5. The method of claim 1, wherein said pharmaceutically acceptable salt of a carboxylic acid group is a sodium salt or a potassium salt.

6. The method of claim 1, wherein the alkyl groups are $C_1$–$C_6$ alkyl groups and the alkoxy group is a $C_1$–$C_6$ alkoxy group.

7. The method of claim 1, wherein said inhibitor of the protein tyrosine kinase pathway is genistein.

8. The method of claim 1, wherein said choroidal neovascularization is that which results from macular degeneration.

9. The method of claim 1, wherein said choroidal neovascularization is that which has been treated, is being treated or will be treated with laser photocoagulation.

10. The method of claim 1, wherein said choroidal neovascularization is that which has been treated, is being treated or will be treated with photodynamic therapy.

11. The method of claim 1, wherein said choroidal neovascularization is choroidal neovascularization that persists or recurs after surgical removal of an existing choroidal neovascularization.

12. The method of claim 1, wherein said choroidal neovascularization is that which results from histoplasmosis.

13. The method of claim 1, wherein said choroidal neovascularization is that which results from pathological myopia.

14. The method of claim 1, wherein said choroidal neovascularization is that which results from angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida* endophthalmitis, extrapapillary hamartomas of the retinal pigmented epithelium, fundus flavimaculatus, idiopathic, macular hold, malignant melanoma, membranproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctate inner choroidopathy, radiation retinopathy, retinal cryoinjury, retinitis pigmentosa, retinochoroidal coloboma, rubella, sarcoidosis, serpoiginous or geographic choroiditis, subretinal fluid drainage, tilted disc syndrome, *Taxoplasma* retinochoroiditis, tuberculosis, or Vogt-Koyanagi-Harada syndrome.

15. The method of claim 10, wherein said choroidal neovascularization is that which results from macular degeneration.

16. The method of claim 15, wherein genistein is administered systemically.

17. The method of claim 16, wherein genistein is administered in an amount from about 1 mg/kg/day to about 100 mg/kg/day.

18. The method of claim 17, wherein genistein is administered in an amount from about 15 mg/kg/day to about 50 mg/kg/day.

19. The method of claim 16, wherein genistein is administered orally or by injection.

20. The method of claim 10, wherein said choroidal neovascularization is that which has been treated, is being treated or will be treated with laser photocoagulation.

21. The method of claim 20, wherein genistein is administered topically, subconjunctivally, retrobulbarly, periocularly, subretinally, suprachoroidally, or intraocularly.

22. The method of claim 21, wherein genistein is administered by a mechanical reservoir, device or implant.

23. The method of claim 21, wherein genistein is administered intraocularly in an amount from about 0.1 mg total to about 5 mg total.

24. The method of claim 23, wherein genistein is administered intraocularly in an amount from about 0.5 mg total to about 1 mg total.

25. The method of claim 10, wherein genistein is administered topically, subconjunctivally, retrobulbarly, periocularly, subretinally, suprachoroidally, or intraocularly.

26. The method of claim 25, wherein genistein is administered by a mechanical reservoir, device or implant.

27. The method of claim 25, wherein genistein is administered intraocularly in an amount from about 0.1 mg total to about 5 mg total.

28. The method of claim 27, wherein genistein is administered intraocularly in an amount from about 0.5 mg total to about 1 mg total.

29. The method of claim 10, wherein said choroidal neovascularization is choroidal neovascularization that persists or recurs after surgical removal of an existing choroidal neovascularization.

30. The method of claim 29, wherein genistein is administered topically, subconjunctivally, retrobulbarly, periocularly, subretinally, suprachoroidally, or intraocularly.

31. The method of claim 30, wherein genistein is administered by a mechanical reservoir, device or implant.

32. The method of claim 30, wherein genistein is administered intraocularly in an amount from about 0.1 mg total to about 5 mg total.

33. The method of claim 32, wherein genistein is administered intraocularly in an amount from about 0.5 mg total to about 1 mg total.

34. The method of claim 10, wherein said choroidal neovascularization is that which results from histoplasmosis.

35. The method of claim 10, wherein said choroidal neovascularization is that which results from pathological myopia.

36. The method of claim 10, wherein said choroidal neovascularization is that which results from angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida* endophthalmitis, extrapapillary hamartomas of the retinal pigmented epithelium, fundus flavimaculatus, idiopathic, macular hold, malignant melanoma, membranproliferative glomerulonephritis (type II), metallic intraocular foreign body, morning glory disc syndrome, multiple evanescent white-dot syndrome (MEWDS), neovascularization at ora serrata, operating microscope burn, optic nerve head pits, photocoagulation, punctate inner choroidopathy, radiation retinopathy, retinal cryoinjury, retinitis pigmentosa, retinochoroidal coloboma, rubella, sarcoidosis, serpoiginous or geographic choroiditis, subretinal fluid drainage, tilted disc syndrome, *Taxoplasma* retinochoroiditis, tuberculosis, or Vogt-Koyanagi-Harada syndrome.

* * * * *